United States Patent  
Waycott et al.

(10) Patent No.: US 11,399,476 B2
(45) Date of Patent: Aug. 2, 2022

(54) RED RADISH CULTIVAR SXT MAJESTIC RED

(71) Applicant: Sensient Colors, LLC, St. Louis, MO (US)

(72) Inventors: William Waycott, San Luis Obispo, CA (US); Vergel C. Concibido, Maryland Heights, MO (US); Jöerg Meyer, St. Charles, MO (US)

(73) Assignee: Sensient Colors, LLC, Saint Louis, MI (US)

( * ) Notice: Subject to any disclaimer, the term of this patent is extended or adjusted under 35 U.S.C. 154(b) by 0 days.

(21) Appl. No.: 16/773,200

(22) Filed: Jan. 27, 2020

(65) Prior Publication Data

US 2020/0236886 A1 Jul. 30, 2020

Related U.S. Application Data

(60) Provisional application No. 62/796,782, filed on Jan. 25, 2019.

(51) Int. Cl.
*A01H 5/10* (2018.01)
*A01H 6/20* (2018.01)

(52) U.S. Cl.
CPC ............... *A01H 5/10* (2013.01); *A01H 6/206* (2018.05)

(58) Field of Classification Search
CPC .................................. A01H 5/06; A01H 6/206
See application file for complete search history.

(56) References Cited

PUBLICATIONS

Fontenot, K., et al., "2018 LSU AgCenter Early Spring Radish Variety Trial", retrieved from //www.lsuagcenter.com/profiles/lblack/articles/page1547673679587. (Year: 2018).*

* cited by examiner

*Primary Examiner* — Weihua Fan
(74) *Attorney, Agent, or Firm* — Quarles & Brady, LLP

(57) ABSTRACT

The invention relates to the red radish cultivar designated SXT MAJESTIC RED. Provided by the invention are the seeds, plants, and derivatives of the red radish cultivar SXT MAJESTIC RED. Also provided by the invention are tissue cultures of the red radish cultivar SXT MAJESTIC RED and the plants regenerated therefrom. Still further provided by the invention are methods for producing red radish plants by crossing the red radish cultivar SXT MAJESTIC RED with itself or another red radish cultivar and plants produced by such methods.

15 Claims, No Drawings

RED RADISH CULTIVAR SXT MAJESTIC RED

This application claims the benefit of priority of U.S. Provisional Application No. 62/796,782 filed Jan. 25, 2019, the disclosure of which is hereby incorporated by reference as if written herein in its entirety.

BACKGROUND OF THE DISCLOSURE

The present invention relates to a new and distinctive red radish cultivar, designated SXT MAJESTIC RED.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, rounder shape, smoother texture, root size, higher seed yield, and improved color.

Choice of breeding or selection methods depends on the mode of plant reproduction, the heritability of the trait(s) being improved, and the type of cultivar used commercially (e.g., $F_1$ hybrid cultivar, pure line cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection, and backcross breeding.

The complexity of inheritance influences choice of breeding method. Backcross breeding is used to transfer one or a few favorable genes for a heritable trait into a desirable cultivar. This approach has been used extensively for the adjustment and selection of morphological characters, color characteristics and simply inherited quantitative characters such as earliness, plant height or seed size and shape. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for use as parents in new commercial cultivars; those still deficient in a few traits may be used as parents to produce new populations for further selection.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of radish breeding is to develop new, unique and superior radish lines. The breeder initially selects and crosses two or more parental lines, followed by repeated self-pollination or selfing and selection, producing many new genetic combinations.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments and with millions of different possible genetic combinations being generated. A breeder of ordinary skill in the art cannot predict the final resulting lines he develops, except possibly in a very gross and general fashion. The same breeder cannot produce the same cultivar twice by using the same original parents and the same selection techniques. This unpredictability results in the expenditure of large research funds to develop a superior new radish inbred line.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., *Theor. Appl. Genet.* 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Descriptions of other breeding methods that are commonly used for different traits and crops can be found in one of several reference books (e.g., Allard, *Principles of Plant Breeding*, John Wiley and Son, pp. 115-161 (1960), Fehr (1987)).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization.

The testing preceding release of a new cultivar should take into consideration research and development costs as well as technical superiority of the final cultivar. For seed-propagated cultivars, it must be feasible to produce seed easily and economically.

Radish is an important and valuable vegetable crop. Thus, a continuing goal of radish plant breeders is to develop stable, high yielding radish varieties with desirable characteristics. To accomplish this goal, the radish breeder must select and develop radish plants that have the traits that result in superior parental lines.

The foregoing examples of the related art and limitations related therewith are intended to be illustrative and not exclusive. Other limitations of the related art will become apparent to those of skill in the art upon a reading of the specification.

DETAILED DESCRIPTION OF THE DISCLOSURE

Definitions

In the description and tables which follow, a number of terms are used. In order to provide a clear and consistent understanding of the specification and claims, including the scope to be given such terms, the following definitions are provided.

The allele is any of one or more alternative forms of a gene, all of which relate to one trait or characteristic. In a diploid cell or organism, the two alleles of a given gene occupy corresponding loci on a pair of homologous chromosomes.

A plant having a decreased vigor in the present invention is a plant that, compared to other plants has a less vigorous appearance for vegetative and/or reproductive characteristics including shorter plant height, color or other characteristics.

A plant having essentially all of the physiological and morphological characteristics means a plant having the physiological and morphological characteristics of the recurrent parent, except for the characteristics derived from the converted gene.

Gene converted or conversion plants refers to plants which are developed by a plant breeding technique called backcrossing wherein essentially all the morphological and physiological characteristics of an inbred are recovered in addition to the one or more genes transferred into the inbred via the backcrossing technique, via genetic engineering or mutation. This also includes transference of one or more loci.

Percent identity as used herein refers to the comparison of the homozygous alleles of two radish varieties. Percent identity is determined by comparing a statistically significant number of the homozygous alleles of two developed varieties. For example, a percent identity of 90% between radish variety 1 and radish variety 2 means that the two varieties have the same allele at 90% of their loci.

Percent similarity as used herein refers to the comparison of the homozygous alleles of a radish variety such as SXT MAJESTIC RED with the alleles of another radish plant, and if the homozygous alleles of SXT MAJESTIC RED matches at least one of the alleles from the other plant then they are scored as similar. Percent similarity is determined by comparing a statistically significant number of loci and recording the number of loci with similar alleles as a percentage. A percent similarity of 90% between SXT MAJESTIC RED and another radish plant means that SXT MAJESTIC RED matches at least one of the alleles of the other plant at 90% of the loci.

Plant cell, as used herein includes plant cells whether isolated, in tissue culture, or incorporated in a plant or plant part.

This is a measure of the height of the plant, from the ground to the top of the uppermost leaf, and is measured in centimeters.

As used herein, the term "plant parts" (or a radish plant, or a part thereof) includes but is not limited to protoplasts, callus, leaves, stems, roots, root tips, anthers, pistils, seed, embryos, pollen, ovules, cotyledon, hypocotyl, flower, shoot, tissue, petiole, cells, meristematic cells and the like.

As used herein, progeny includes an $F_1$ radish plant produced from the cross of two radish plants where at least one plant includes radish cultivar SXT MAJESTIC RED. Progeny further includes but is not limited to subsequent F2, F3, F4, F5, F6, F7, F8, F9 and F10 generational crosses with the recurrent parental line.

Quantitative trait loci refer to genetic loci that control to some degree numerically representable traits that are usually continuously distributed.

A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International Convention for the Protection of New Varieties of Plants)

All cultivated forms of radish belong to the family Cruciferae (alt. Brassicaceae) and are grown for their edible hypocotyl. Radishes have been cultivated for thousands of years in both China and the Mediterranean areas. Generally, commercial radishes are grown wherever environmental conditions permit the production of an economically viable yield.

Radish is a quick growing, primarily annual, cool season root vegetable that matures in 3 to 6 weeks. The seed will germinate in 3 to 4 days with soil temperatures of 18° C. to 30° C., but germination rates decline sharply when the soil temperatures fall below 13° C. The best quality and root shape are obtained when the crop grows and matures at moderate temperatures of 10° C. to 30° C. in intermediate to short day lengths. When grown in hot weather, radishes tend to elongate, develop poor shape or no edible hypocotyl at all, and become more pungent. When grown in cold weather, radish tops grow larger and taller, while long days induce flowering or bolting. Thus, growth must be continuous and rapid for good quality. Radishes remain in prime condition only for a few days, as the edible hypocotyl remains in marketable condition only a short time before becoming pithy.

The radish (*Raphanus sativus*) is an extremely variable vegetable. Some radishes are annuals, little more than 4 inches (10 cm) tall at maturity, and some are biennials, going to seed in their second growing season, and topping out at over 6 ft (1.8 m) in height. Most radish types are grown for their enlarged roots, and there is great variation in size, shape and color. The colors of the outer skin can vary widely among the various radishes from red, pink, purple, white, white with green shoulders, green, yellow, red with a white tip up to black skins. The flesh can vary also with most having white flesh, but some having pink or red flesh. The shape can also vary from round, round elongated, rat-tailed and long types.

When looking at the size, the radishes can be small-sized globe or round radishes with a size from 1 to 1.5 inches up to 4 to 5 inches, small long types with roots up to 4 inches, small rat-tailed roots up to 5 inches and the big long-sized "Daikon" types which can grow up to 18 inches.

EXAMPLES

Example 1

Red Flesh Daikon Radish Cultivar SXT MAJESTIC RED

Cultivar (cv.) SXT MAJESTIC RED as described is a red flesh daikon radish cultivar selected for large root size and red colored flesh. In replicated field trials, cv. SXT MAJESTIC RED was compared to cv. Summer Cross No. 3, the most similar cultivar, for eight distinct characters as shown in Table 1. Trial results indicated that the exterior and interior root color of SXT MAJESTIC RED were red, while the color for the same traits of cv. Summer Cross No. 3 were white. The root shape for cv. SXT MAJESTIC RED was consistently oval, while the shape of Summer Cross No. 3 roots was repeatedly elongated and tapered. Cv. SXT MAJESTIC RED also differed from cv. Summer Cross No. 3 for average root length and width. Roots of cv. SXT MAJESTIC RED were shorter and wider, while roots of cv. Summer Cross No. 3 were longer and more slender. Cv. SXT MAJESTIC RED was also faster to flower than Summer Cross No. 3, measured by the number of days from emergence to the initiation of stem elongation at 10 cm.

In addition to root color and shape differences, the data presented here are statistically different at the 95% confidence level, exhibiting a range of means for root length from 26.7 cm to 29.4 cm for cv. SXT MAJESTIC RED and from 34.5 cm to 37.1 cm for cv. Summer Cross No. 3, a range of means for root width from 11.0 cm to 12.6 cm for cv. SXT MAJESTIC RED and from 5.7 cm to 6.9 cm g for cv. Summer Cross No. 3, and a range of means for stem length elongation (days from emergence to 10 cm) from 74.5 days to 76.5 days for cv. SXT MAJESTIC RED and from 84.2 day to 87.8 days for cv. Summer Cross No. 3, respectively. Therefore, these measurements for root length and width, and stem elongation, in addition to root color and shape, illustrate that cv. SXT MAJESTIC RED was significantly different than its most similar variety, cv. Summer Cross No. 3, in field trials conducted in 2017 and 2018.

Deposit Information: In accordance with 37 C.F.R. §§ 1.801-1.809, a representative sample of seeds of red radish cultivar Red Radish SXT Majestic Red has been deposited with the American Type Culture Collection (ATCC), 10801 University Boulevard, Manassas, VA 20110-2209 on Mar. 7, 2022, and has been assigned Accession No. PTA-127278.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

TABLE 1

Evaluation of cv. SXT MAJESTIC RED and the most similar cultivar, cv. Summer Cross No. 3, for several important characters.

| Trial No | Cultivar | Rep No. | Exterior Root Color[a] | Interior Root Color[b] | Root Shape[c] | Ave. Root Length[d] | Ave. Root Width[e] | Ave. Root Weight[f] | Days to Bolting[g] | Shoot Fresh Weight[h] |
|---|---|---|---|---|---|---|---|---|---|---|
| Trial 1: | cv. SXT | Rep. 1 | Red | Red | Oval | 27.2 ± 1.6 | 10.1 ± 1.0 | 483 ± 20.2 | 74 ± 1.3 | 652 ± 43.8 |
| Evaluated | Majestic | Rep. 2 | Red | Red | Oval | 29.4 ± 1.8 | 12.4 ± 0.9 | 454 ± 19.8 | 76 ± 1.2 | 641 ± 42.7 |
| 15 Aug. 2017 | Red: | Average: | Red | Red | Oval | 28.3 ± 1.7 | 11.3 ± 1.0 | 469 ± 20.0 | 75 ± 1.3 | 647 ± 43.2 |
| Nipomo, CA | cv. Summer | Rep. 1 | White | White | Tapered | 35.6 ± 1.8 | 5.1 ± 0.7 | 444 ± 18.1 | 83 ± 1.7 | 661 ± 46.5 |
| | Cross No. 3: | Rep. 2 | White | White | Tapered | 37.4 ± 1.7 | 6.8 ± 0.8 | 485 ± 19.4 | 86 ± 1.5 | 639 ± 45.8 |
| | | Average: | White | White | Tapered | 36.5 ± 1.8 | 6.0 ± 0.8 | 465 ± 18.8 | 84.5 ± 1.6 | 650 ± 46.2 |
| Trial 2: | cv. SXT | Rep. 1 | Red | Red | Oval | 26.6 ± 1.8 | 11.3 ± 0.9 | 448 ± 21.6 | 77 ± 1.3 | 665 ± 53.2 |
| Evaluated | Majestic | Rep. 2 | Red | Red | Oval | 28.9 ± 1.5 | 13.3 ± 0.9 | 473 ± 20.3 | 75 ± 1.3 | 610 ± 54.7 |
| 6 Nov. 2018 | Red: | Average: | Red | Red | Oval | 27.8 ± 1.7 | 12.3 ± 0.9 | 461 ± 21.0 | 76 ± 1.3 | 638 ± 54.0 |
| Nipomo, CA | cv. Summer | Rep. 1 | White | White | Tapered | 33.1 ± 1.5 | 7.7 ± 0.8 | 445 ± 20.4 | 88 ± 1.7 | 644 ± 51.9 |
| | Cross No. 3: | Rep. 2 | White | White | Tapered | 37.0 ± 1.6 | 5.4 ± 0.8 | 478 ± 19.4 | 89 ± 1.6 | 679 ± 52.6 |
| | | Average: | White | White | Tapered | 35.1 ± 1.6 | 6.6 ± 0.8 | 462 ± 19.9 | 88.5 ± 1.7 | 662 ± 51.3 |
| Range of variation among means of statistically significant difference at the 95% level using the confidence interval [CI = mean ± (SD × SE)]: | | | | | | | | | | |
| | cv. SXT MAJESTIC RED | | Sig. | Sig. | Sig. | 26.7 to 29.4 | 11.0 to 12.6 | Not Sig. | 74.5 to 76.5 | Not Sig. |
| | cv. Summer Cross No. 3 | | Sig. | Sig. | Sig. | 34.5 to 37.1 | 5.7 to 6.9 | Not Sig. | 84.2 to 87.8 | Not Sig. |

[a]Color evaluation of root epidermis
[b]Color evaluation of root cortex
[c]Visual evaluation of root shape.
[d]Mean root length using two sowing dates of 20 plants per replication in centimeters ± standard deviation.
[e]Mean root width using two sowing dates of 20 plants per replication in centimeters ± standard deviation.
[f]Mean root weight using two sowing dates of 20 plants per replication in grams ± standard deviation.
[g]Number of days from emergence to 10 centimeters (stem elongation elongation) ± standard deviation.
[h]Mean shoot weight using two sowing dates of 20 plants per replication in grams ± standard deviation.

What is claimed:

1. A plant of red radish cultivar SXT MAJESTIC RED, wherein representative seed of said red radish cultivar has been deposited under ATCC Accession No. PTA-127278.

2. A plant part of the plant of claim 1, wherein the plant part comprises at least one cell of said plant.

3. A seed of red radish cultivar SXT MAJESTIC RED, wherein representative seed of said red radish cultivar SXT MAJESTIC RED has been deposited under ATCC Accession No. PTA-127278.

4. A method of producing red radish seed, the method comprising crossing the plant of claim 1 with itself or a second red radish plant to produce said red radish seed.

5. The method of claim 4, the method further comprising crossing the plant of red radish cultivar SXT MAJESTIC RED with a second, non-isogenic red radish plant to produce said red radish seed.

6. An $F_1$ red radish seed produced by the method of claim 5.

7. A red radish plant produced by growing the $F_1$ red radish seed of claim 6.

8. A composition comprising the seed of claim 3 comprised in plant seed growth media.

9. The composition of claim 8, wherein the plant seed growth media is soil or a synthetic cultivation medium.

10. A plant of red radish cultivar SXT MAJESTIC RED further comprising a single locus conversion, wherein said plant otherwise comprises all of the morphological and physiological characteristics of said red radish cultivar when grown under the same environmental conditions, and wherein representative seed of said red radish cultivar have been deposited under ATCC Accession No. PTA-127278.

11. A seed that produces the plant of claim 10.

12. The seed of claim 11, wherein the single locus confers a trait selected from the group consisting of increased anthocyanin content, increased flower size, multiple petals, broad environmental adaptation, and insect and pest resistance, and resistance to bacterial, fungal, or viral disease.

13. The method of claim 5, the method further comprising:
 a. crossing a plant grown from said red radish seed with itself or a different red radish plant to produce seed of a progeny plant of a subsequent generation;
 b. growing a progeny plant of a subsequent generation from said seed of a progeny plant of a subsequent generation and crossing the progeny plant of a subsequent generation with itself or a second plant to produce seed of a progeny plant of a further subsequent generation; and
 c. repeating step (b) with sufficient inbreeding to produce seed of an inbred red radish plant that is derived from red radish cultivar SXT MAJESTIC RED.

14. A method of producing a commodity plant product, the method comprising producing the commodity plant product from the plant of claim 1.

15. The method of claim 14, wherein the commodity plant product is anthocyanin.

* * * * *